US006528763B1

(12) United States Patent
Lahram et al.

(10) Patent No.: US 6,528,763 B1
(45) Date of Patent: Mar. 4, 2003

(54) LASER SEARCH PEENING FOR EXFOLIATION CORROSION DETECTION

(75) Inventors: David F. Lahram, Powell, OH (US); Allan H. Clauer, Worthington, OH (US); Jeff L. Dulaney, Dublin, OH (US)

(73) Assignee: LSP Technologies, Inc., Dublin, OH (US)

( * ) Notice: Subject to any disclaimer, the term of this patent is extended or adjusted under 35 U.S.C. 154(b) by 23 days.

(21) Appl. No.: 09/846,084

(22) Filed: Apr. 30, 2001

(51) Int. Cl.$^7$ ............................................ B23K 26/00
(52) U.S. Cl. .............................. 219/121.85; 219/121.6
(58) Field of Search ................. 219/121.85, 121.84, 219/121.83, 121.61, 121.6

(56) References Cited

U.S. PATENT DOCUMENTS

| | | | | |
|---|---|---|---|---|
| 3,911,733 A | * | 10/1975 | Bhuta et al. | 356/35.5 |
| 4,084,427 A | * | 4/1978 | Jacoby et al. | 356/32 |
| 4,564,743 A | * | 1/1986 | Birley et al. | 219/121.14 |
| 5,065,630 A | * | 11/1991 | Hadcock et al. | 73/802 |
| 5,376,793 A | * | 12/1994 | Lesniak | 250/330 |
| 5,549,768 A | * | 8/1996 | Mahoney | 148/695 |
| 5,549,803 A | * | 8/1996 | Schoess et al. | 204/400 |
| 5,682,236 A | * | 10/1997 | Trolinger et al | 356/28.5 |
| 5,698,787 A | * | 12/1997 | Parzuchowski et al. | 73/583 |
| 5,760,904 A | * | 6/1998 | Lorraine et al. | 356/513 |
| 6,000,844 A | * | 12/1999 | Cramer et al. | 374/124 |
| 6,013,873 A | * | 1/2000 | Daito et al. | 136/243 |
| 6,182,512 B1 | * | 2/2001 | Lorraine | 73/602 |
| 6,191,385 B1 | * | 2/2001 | O Loughlin e al. | 219/121.6 |
| 6,285,183 B1 | * | 9/2001 | Collingwood et al. | 324/202 |
| 6,341,936 B1 | * | 1/2002 | Cowie et al. | 29/889.1 |
| 6,378,387 B1 | * | 4/2002 | Froom | 73/865.8 |

OTHER PUBLICATIONS

*Standard Test Method for Exfoliation corrosion Susceptibility in 2XXX and 7XXX Series Aluminum Alloys* (*EXCO Test*), ASSTM Designation: G 34–99, pp. 124–130 no date available.

* cited by examiner

*Primary Examiner*—Tom Dunn
*Assistant Examiner*—Zidia Pittman
(74) *Attorney, Agent, or Firm*—Randall J. Knuth

(57) ABSTRACT

An exfoliation corrosion detection method which enables rapid detection and evaluation of hidden exfoliation corrosion on aircraft with related cost savings. Pressure exerted on the surface by the laser created plasma generates a pressure pulse or shock wave that propagates into the part. When the stress in the shock wave is above the dynamic elastic limit of the material, the surface material yields plastically. This plastic strain creates compressive residual stresses in the surface, thereby enabling detection of exfoliation corrosion, if present.

22 Claims, 4 Drawing Sheets

LASER SEARCH PEENING FOR EXFOLIATION CORROSION DETECTION

BACKGROUND OF THE INVENTION

1. Field of the Invention

The present invention relates to the detection of exfoliation corrosion in metal structures, and in particular, to a method for detecting exfoliation corrosion in the aluminum wing and fuselage sections of aircraft structures.

2. Description of the Related Art

Over the years, many different nondestructive evaluation methods or inspection techniques have been used such as electromagnetic, thermal, ultrasonic, radiographic and optical methods to inspect for hidden cracks or corrosion in the wing and fuselage sections of aircraft.

Exfoliation corrosion refers to the physical appearance of a specific type of intergranular corrosion which is layered or leafed in character and consists of alternating strata of corroding and non-corroding metal. It typically occurs in high-strength aluminum-alloy rolled sheet or plate which has a laminar-like microstructure consisting of grains flattened in the plane of the sheet or plate. The exfoliation or corrosion attack occurs along the grain boundaries in the rolling plane and predominantly in the rolling direction of the aluminum sheet or plate.

Exfoliation corrosion is a very common form of corrosion in precipitation-hardened 7XXX series aluminum alloy (AL—Sm—Mg) wrought products. Precipitation hardening, the process used to heat-treat aluminum alloys to the -T6 condition, tends to produce a somewhat continuous precipitate of Al—Zn, Al—Mg, and Mg—Zn intermetallic compounds in the grain boundaries of this series of alloys. These intermetallic compounds have an electrochemical potential anodic to the surrounding aluminum, hence causing them to preferentially corrode in certain corrosive environments. With the relative area of cathode (surrounding grains) to anode (small intermetallic particles) being quiet large, this attack can progress very rapidly with the grain boundary corrosion product wedging or separating the grains apart and causing the uncorroded material to lift or leaf. This effect produces the characteristic "blister" appearance of exfoliation. Current generation aluminum alloys, 7050 and 7150, exhibit high strengths in -T6-type tempers and when they are processed to the -T76, -T74 or -T73-type temper, to improve their resistance to stress corrosion cracking and/or exfoliation corrosion although this improvement is often achieved at some cost to strength vis-a-vis the -T6 condition. However, using these tempers does not resolve the exfoliation corrosion problem for aluminum alloys, such as, 7178-T6 still in use today that were produced prior to this current generation of alloys.

The typical aircraft application for these alloys is on the upper wing skins where failure originating from exfoliation corrosion is a significant concern to prevent failure of the wing structure. Exfoliation corrosion detection is required for early and accurate detection on all aircraft. The exfoliation corrosion is sometimes evident on the surface of the wing as it can cause the paint coating to have a blistered appearance in the corroded areas. When detected, these areas are sanded to remove the gross exfoliation corrosion until it is no longer visually observable. However, exfoliation corrosion can still be present in the sanded areas that is not visually observable even at higher magnifications. It may also be present in areas where exfoliation corrosion was not previously observed and is not detectable on the surface. This "hidden exfoliation" occurs when the amount of corrosion products between the grains is relatively small and has not caused the grains above the corroded boundaries to lift or separate from the subsurface grains.

Over the years, many different NDE methods or inspection techniques (electromagnetic, thermal, ultrasonic, radiographic and optical) have been developed and used to inspect for hidden cracks or corrosion in the wing and fuselage sections of aging aircraft. Each of these candidate techniques has its own inherent performance and detection limitations; therefore, new techniques or tools are being developed and validated for both production and field use to improve detection capability and reliability, and to reduce the cost of inspection.

Inspection for hidden exfoliation corrosion is typically conducted, for example, on the aircraft upper wing surface around fastener holes. The fastener holes are sometimes filled with steel rivets and a galvanic cell is created between the surface of the steel rivet and the surface of the hole in the aluminum wing skin, accelerating the rate of corrosion along the grain boundaries from the surface of the hole. There are several methods to locate the hidden exfoliation corrosion, but the current method utilizes a glass bead shot peening method and is called a search peening process. This search peening process is up to 95% efficient in detecting exfoliation corrosion. Once an area of corrosion has been detected, the area is sanded until the exfoliation corrosion is no longer visible in the sanded area. The area is then again glass bead search peened and inspected for additional exfoliation corrosion, revealed by the bead peening. This process is repeated until no more hidden exfoliation is detected after glass bead search peening.

Glass bead peening for inspection for exfoliation corrosion works by producing a compressive residual stress and cold work into the metal surface being inspected. These effects cause the surface material in areas having underlying grain boundary corrosion to exfoliate, i.e., blister or "leaf up," and thereby expose only underlying corrosion. If there is no underlying corrosion, exfoliation does not occur.

Although generally effective, this method for exfoliation corrosion detection has several drawbacks. For example, it takes a significant amount of time to isolate the wing being search peened to contain the peening media and also to extricate the glass bead media from the surface being inspected. These requirements add three to six days to the Program Depot Maintenance (PDM) cycle for an aircraft. In addition to the added time, the additional workload increases the cost for maintenance of the aircraft.

Accordingly, the need exists for a cost-effective and time-efficient exfoliation corrosion detection apparatus and method which enables rapid inspection and evaluation of significant portions of the aircraft for exfoliation corrosion.

SUMMARY OF THE INVENTION

The present invention satisfies that need by providing an exfoliation corrosion detection method that enables rapid inspection for the detection and evaluation of exfoliation corrosion on aircraft with related cost savings.

The present invention utilizes laser shock peening to produce the compressive residual stresses and cold work into the metal surface, necessary to expose hidden exfoliation corrosion. Laser shock peening is currently being used in production to produce deep compressive residual stresses in titanium compressor blades and now this same technology can be adapted to search peening. The depth and magnitude of residual compressive stresses can be tailored by the application of specific overlays and controlling the intensity of the laser beam.

In the laser shock peening process, the surface of the part is first covered with two types of overlays, one transparent to the laser beam and the other opaque to the laser beam. The opaque overlay is applied directly to the surface of the part. The opaque overlay is typically paint or tape and has three functions. The first function is to protect the surface of the part from the intense heat of the plasma plume generated during the laser shock peening process. The second function is to enhance the strength of the shock wave from the plasma. The third and final function is to provide a consistent processing medium for the laser beam to couple to. The transparent overlay is typically water and is applied over the opaque overlay. The primary function of the transparent layer is to confine the plasma plume against the surface of the part in order to generate higher peak pressures during the laser shock peening process.

When the laser is fired, the laser beam passes through the transparent overlay and strikes the opaque overlay. When the laser beam strikes the opaque overlay, it initially vaporizes some of the opaque material surface. The rest of the laser beam is absorbed by the vaporized material and creates a plasma. The expanding plasma is confined between the transparent overlay and the surface of the part. As a result, high pressures up to 1,400,000 psi are generated in the confined plasma. The pressure exerted on the surface by the confined plasma generates a pressure pulse or shock wave that propagates into the metallic part. When the stress in the shock wave is above the dynamic elastic limit of the material, the surface material yields plastically. This plastic strain creates residual compressive stresses in the surface.

By varying the laser beam parameters and type of overlays, the magnitude and depth of the residual stresses may be controlled. Consequently, laser shock peening can be used to expose and identify hidden exfoliation corrosion, replacing the current search peening method that bombards the surface with glass beads.

Important parameters to the laser search peening process are the search pattern and the shape of the laser beam spot when searching around holes or along edges for exfoliation corrosion. The laser spot is the area laser peened by one pulse of the laser beam. One type of search pattern is a circular search pattern that can be used for laser search peening around holes, such as fastener holes. Another type of circular search pattern is a spiral or spiral. The third type of circular search pattern is a pattern of concentric rings. For these types of search patterns, individual laser spots are incremented a specific distance from either the edge of the hole or from the previous spot or from both the edge of the hole and from the previous spot. The laser beam spots may or may not overlap a neighboring spot. A single doughnut-shaped laser spot may be used to encircle a hole to provide up to 100 percent peening coverage of the desired search area, provided the power density is sufficient to introduce the needed residual stresses. Alternatively, the use of multiple laser spots may be needed to achieve 100 percent coverage of the desired area depending on the laser spot shape. The shape of the laser beam spot on the part may have many other configurations. The shape may be round, square or elliptical, or other variations, in addition to the doughnut or equivalent shape. Each of these shapes may be used to provide the most efficient laser search peening.

In addition to searching around holes, areas near other types of machined or cut edges can also contain exfoliation corrosion. Three search patterns can be used for searching these areas. The first type of search pattern is a laser spot straddling a joint or edge to simultaneously search peen the surface on both sides of the joint or edge. The second type of search pattern is to search peen with individual laser spots on each side of the joint. Finally, laser spots on one side only can be used if only one side is to be inspected. The shape of the laser spots can be of any shape to provide efficient laser search peening.

The laser search peen process may be automated by mounting the laser search peen equipment on a remotely controlled robotic vehicle, such as an AutoCrawler M50, wherein the AutoCrawler M50, manufactured by Advance Robotic Vehicles, Inc. of Seattle, Wash., is capable of walking or crawling along the surface of the part being search peened and positioning itself in a specific location. The equipment to be mounted in the robotic vehicle may include the laser delivery head, laser beam effluent removal system, imaging system, and other support systems.

Accordingly, it is an object of the present invention to provide a search peening method which may be applied to exfoliation corroded surfaces of various types, curved or flat.

It is another object of the present invention to provide a search peening method which overcomes the long preparation and cleanup required during the use of the current state of the art glass bead shot peening process.

It is a further object of the present invention to provide a search peening method for detecting hidden exfoliation corrosion with greater precision, accuracy and speed than existing methods.

It is a further object of the present invention to provide a search peening method for detecting hidden exfoliation corrosion, which is easy to use and adaptable for field use.

It is a further object of the present invention to provide a search peening method for detecting hidden exfoliation corrosion where the entire wing structure to be processed will not need to be isolated from the rest of the repair or service facility during the search process.

It is a still further object of the present invention to reduce the time and cost for detecting hidden exfoliation corrosion. These and other objects, features and advantages of the present invention will be apparent from the drawings, detailed description and claims which follow.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification

DETAILED DESCRIPTION OF THE INVENTION

Good exfoliation corrosion resistance is evidenced by an EXCO rating of "EC" or better for aluminum alloys as indicated in ASTM G 34, but in some cases other measures of corrosion resistance may be specified or required by airframe builders, such as stress corrosion cracking resistance or electrical conductivity. Satisfying any one or more of these specifications for new or current build airframes is considered good practice to prevent corrosion resistance. However in those applications where an aluminum alloy was developed prior to the EXCO ratings or the application has been in use far longer than anticipated by the original design, such as older transport aircraft, exfoliation corrosion is an issue that has to be addressed to prevent failure of the component.

Figure 7:
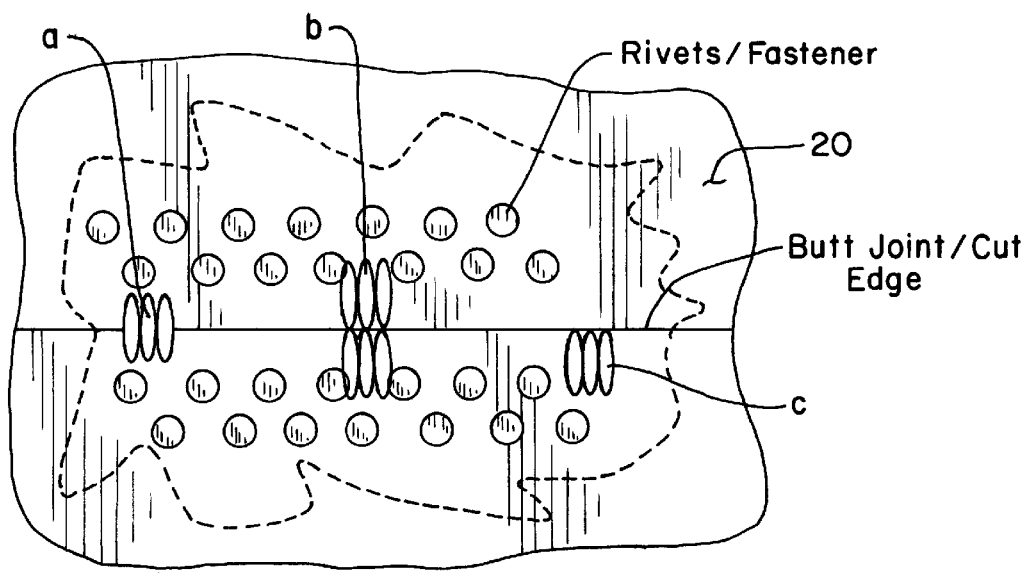
FIG. 7 is a top view of search pattern for butt joints or cut edges.

Referring now to the drawings and particularly to FIG. 7, there is shown the corrosion detection system 10 of the present invention having a laser instrument 12, a laser search peen head 14 connected to said laser instrument, and a controller means 16 connected to control the laser instrument 12, laser search peen head 16, overlay applicator mechanism 13, positioning mechanism 15 and inspection instrument 18. Detection system 10 directs laser search peen head 14 to laser search peen area 22, and during this process, overlay applicator mechanism 13 applies the processing overlay or overlays as sequenced from controller 16, and laser system 12 then delivers a laser pulse to laser search peen head 14. As shown, system 10 is capable of detecting exfoliation corrosion, via camera 18 on significant portions of aluminum alloy plate section 20 as well as other surfaces, by examining the laser search peened surface 22 from low magnification to high magnification depending primarily on the optics and resolution of camera 18. This magnification could be in the range of, for example, 0 to 30× but is not limited to this range. Other detection means, such as direct visual examination of plate 20 or other ways, may also be utilized to perceive and/or confirm exfoliation delamination within the laser spot areas 22. Upon completion of the inspection of area 22 with camera 18 for evidence of exfoliation determination within area 22, the laser system 10, or portion thereof, is indexed to the next area 26 to be laser search peened. The positioning mechanism 15 provides information to controller 16 to index the detection system 10 or laser search peen head 14 from one location 22 to the next location 26.

Figure 1:
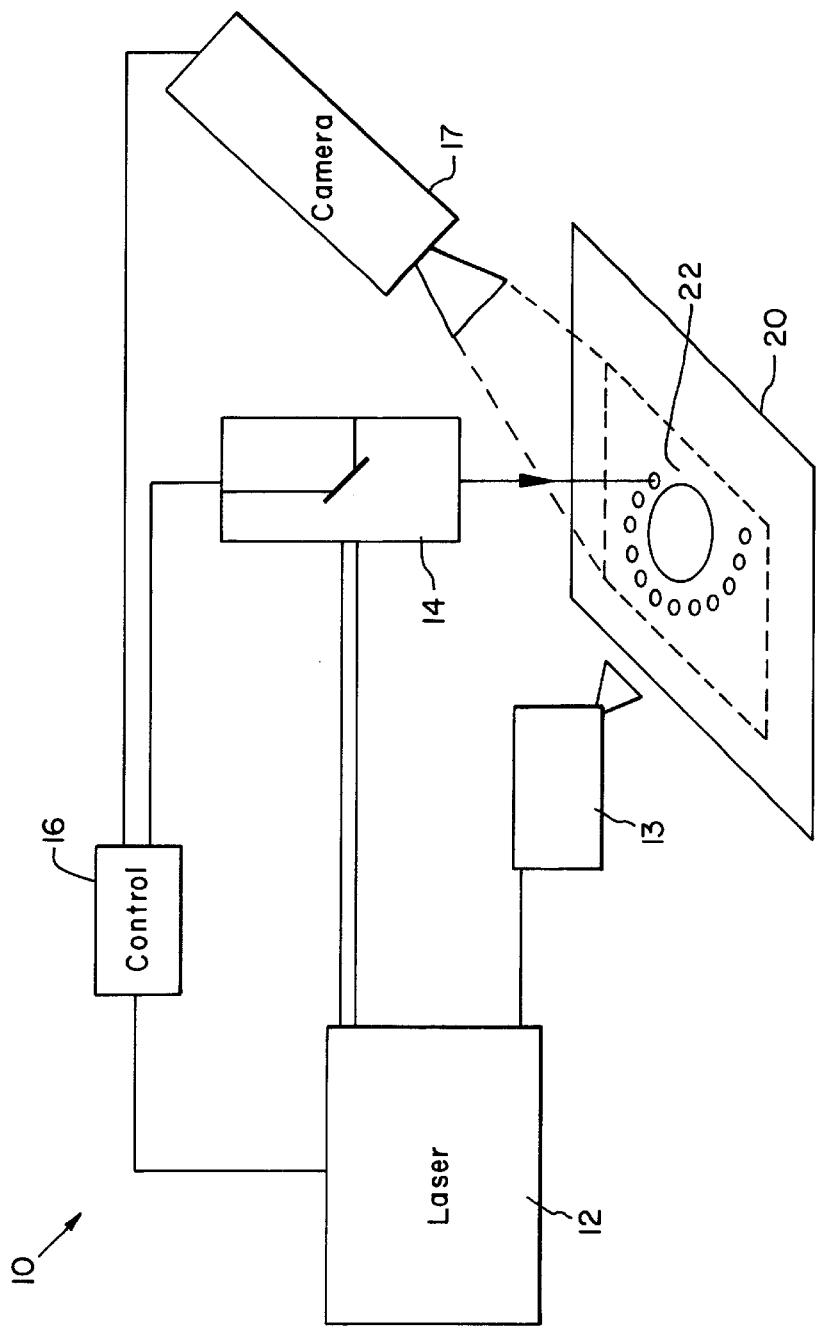
FIG. 1 is one embodiment of the corrosion detection system of the present invention.
Figure 2:
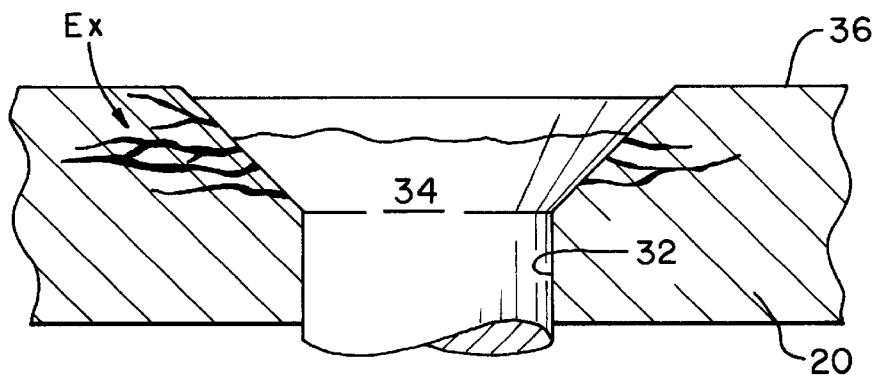
FIG. 2 is a side view showing the location of the hidden exfoliation corrosion detected in aluminum alloy plate around a steel fastener.

FIG. 2 shows a side view of a typical location for exfoliation corrosion around a fastener hole 32 in metal plate 20. The fastener 34 may not be the same metal as the metal plate 20. This arrangement between two dissimilar metals (metal plate 20 and metal fastener 34) creates a galvanic cell when the gap 36 between the metal plate 20 and the fastener 34 is filled with an aqueous solution that is either acidic or basic. The electrochemical potential of the galvanic cell increases the propensity for exfoliation corrosion in metal plate 20. Evidence of exfoliation corrosion or delamination potential is shown at location "EX". Such exfoliation corrosion is typically parallel to the plane of a rolled plate 20, and generally starts from the surface 32 and propagates into plate 20 away from the fastener 34. The non-corroded material between the corroded paths and the surface will lift, or exfoliate, when search peened and thereby become visible on the surface.

The method of use of corrosion detection system 10 is shown in FIGS. 3 to 7. The laser search peen head 14 connected to laser instrument 12 would have the ability of applying a number of particular search patterns to the surface 36 of plate 20.

Figure 3:
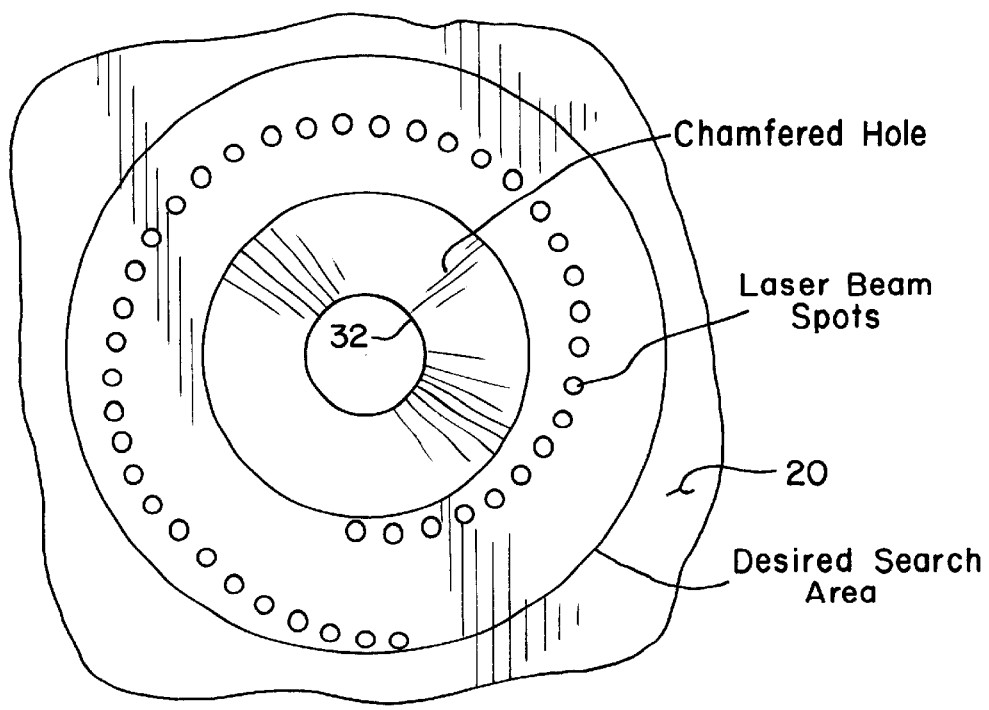
FIG. 3 is a top view of a spiral laser spot search pattern.

These patterns consist of consecutive laser spots that are incremented a specific distance from the edge of the hole or from the previous shot or spot or both. As shown in FIG. 3, a spiral type string of laser beam spots is generated around and radially outward from the edge of hole 32 with an increasing distance from the hole as the location rotates about the hole. In FIG. 3, the laser spots do not overlap the previous spot and are shown to be circular. These two variables need not be the same in all cases, more particularly the spots may overlap and the spots may be of a different shape such as round, square, elliptical, or any other type of desirable spot shape. With this particular search pattern the area about hole 32 may or may not be 100% covered by laser spots. Additionally more than one spiral can be utilized, but offset in radial direction from the previous spiral.

Figure 4:
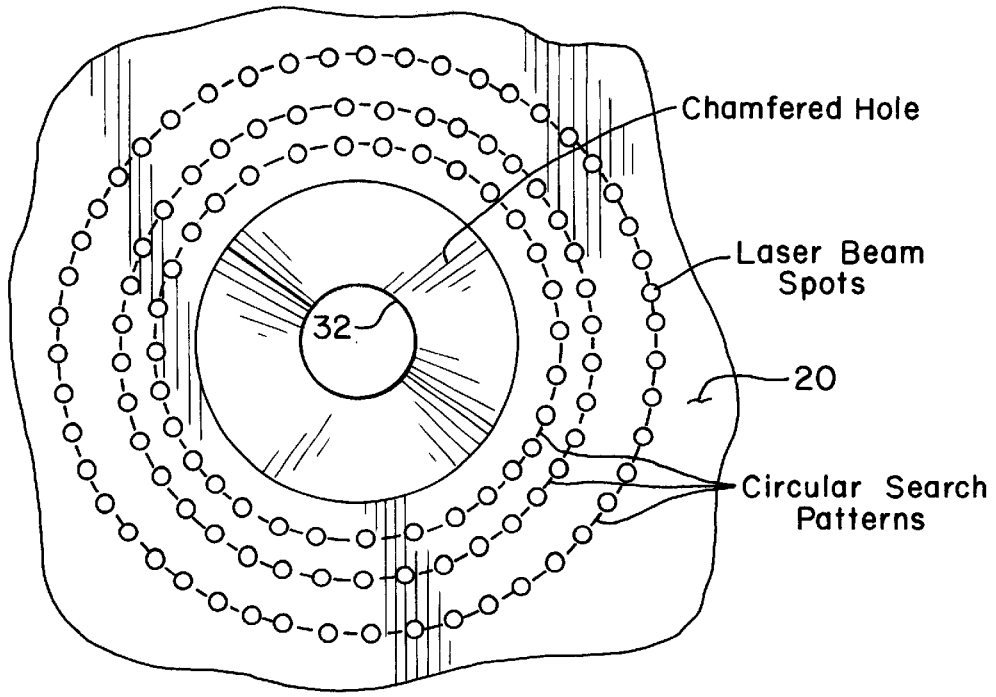
FIG. 4 is a top view of a circular laser spot search pattern.

FIG. 4 shows a search pattern consisting of a series of concentric circular spots located about hole 32. The radius of each circle within the pattern may be different depending upon particular needs of the search.

The search pattern need not be circular or concentric to the hole if larger areas need to be laser search peen inspected for exfoliation corrosion.

Figure 5:
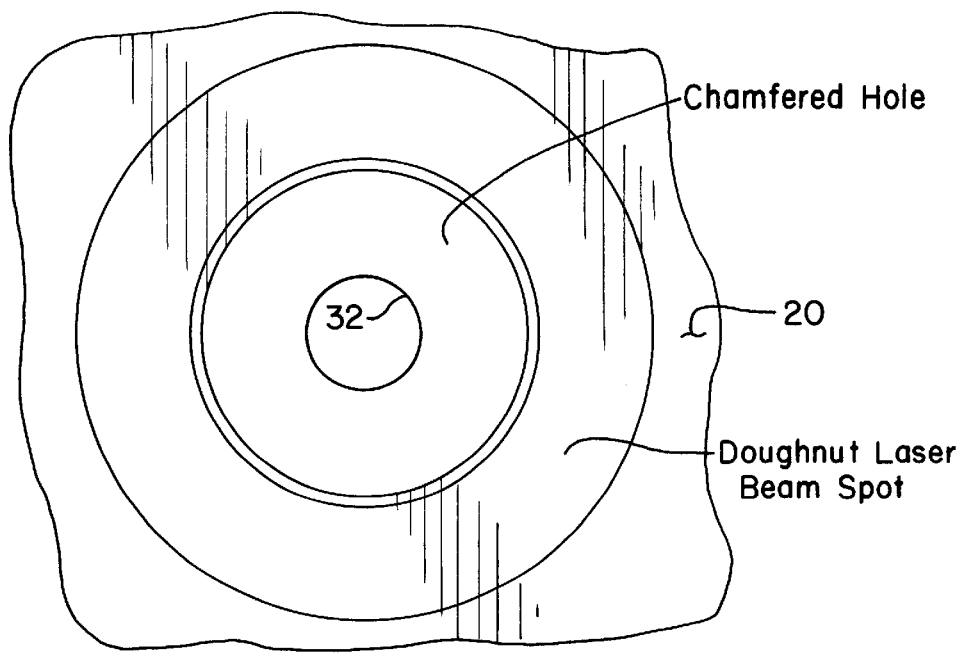
FIG. 5 is a top view of a doughnut-shaped laser spot used when detecting exfoliation corrosion around a hole.

A doughnut-shaped laser beam spot to encircle hole 32 efficiently is shown in FIG. 5, and can provide 100% search peening coverage for the desired area, provided that the power density is sufficient to induce the needed compressive residual stresses to cause the hidden exfoliation corrosion to be revealed. Typical laser beam power densities necessary to detect hidden exfoliation corrosion may range from 0.5 to 9 Gigawatt/cm$^2$ depending upon the composition and properties of plate 20. Typical laser beam sources may be fired at a rate between one half to one hundred Hz; however, the laser beam source may not be limited to this range of frequencies. More efficient processing rates may be achieved at higher frequencies.

Figure 6:
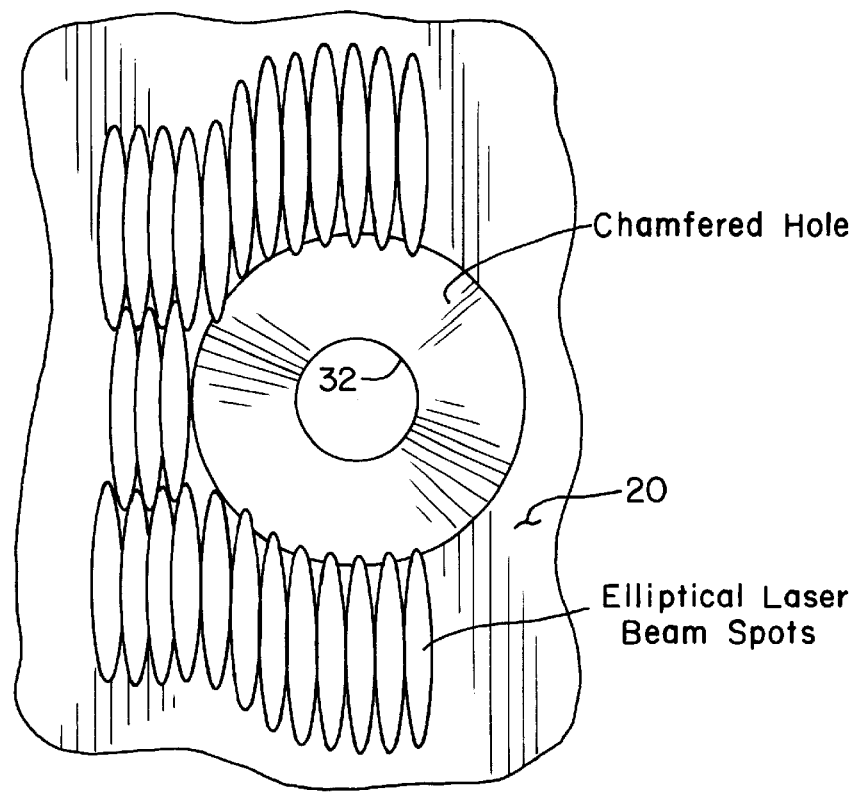
FIG. 6 is a top view of pattern applied around half of the surface surrounding a hole, using elliptical laser spots.

FIG. 35 show the area all around hole 32 being searched. However, the search peened area may extend only partially around the hole, as shown in FIG. 6. FIG. 6 shows a search pattern about a hole with elliptical laser spots with nearly 100% coverage within the pattern. Also within the search pattern, the laser spots do not need to be elliptical. They can be any shape or size that can provide a proper power density and effective pattern for exposing hidden exfoliation corrosion by efficient laser search peening. Laser spots may have an elliptical shape, circular shape, square or rectangular shapes, or other necessary shapes.

A method, in one form of the invention, provides for defining an area 22 on the surface for corrosion inspection, then applying the transparent or opaque overlay or both to the surface 36 of the area 22 to be laser search peened. The next step includes projecting a laser beam onto a portion of the area 22, forming a laser beam spot on the surface, and generating a pressure pulse in the material resulting in compressive residual stresses in the surface. After the laser spot or spots have been applied, a means for examining the area of the surface for evidence of exfoliation corrosion either via camera 18, a photograph, or direct visual examination is needed.

Such investigation or examination of the surface after the resulting compressive residual stresses have been created would, in the presence of exfoliation corrosion, show the characteristic blistered appearance caused by the delamination of the exfoliated material.

Although this method would be sufficient for determining exfoliation corrosion around fasteners 36, other potential locations for exfoliation corrosion, as shown in FIG. 7, include butt joints, edge cuts, or other types of edges where exfoliation corrosion can initiate and progress into the plate from the cut surface, but lie underneath the visible surface. FIG. 7 shows three different search patterns that can be used along edge cuts, such as where two plates engage each other to form a butt joint. Location "A" shows laser spots applied along the adjoining edges of the two plates with each spot straddling the joint; while search pattern "B" shows laser beam spots applied on separately to each of the adjoining plates; while test pattern "C" shows laser beam spots applied on only one of the two or more plates. Although previously it has been inferred that the laser spots are located directly over the areas in which exfoliation corrosion may occur, such may not be the case in particular instances. For example, the laser search peening is applied to one side of the plate, while evidence of the corrosion, i.e., blistering may be visually evident or perceivable on another side thereof, for example on the surface of the plate opposite the laser search peened surface. In such case, the area at which corrosion inspection is occurring is separate and different than the area to which the laser beam is projected or applied.

Once exfoliation corrosion has been determined to be located within a particular area, means for removing the exfoliation corrosion can be applied to the area to bring the part back within specifications.

For automating the system, the search peening system may be mounted on an equipment such as a remotely controlled robot which would be able to traverse along the surfaces 20 of the part to be laser search peened, such as along an aircraft wing, or other area. Mounted on such traversing robot would be the searching peening mechanism 10 or a portion thereof, along with a means for applying the overlays such as a transparent and opaque overlay applicator 13 along with the means for visualizing any delamination, such as a camera 18. Mounted on such a robot could also be the means for focusing the laser beam 14, positioning the system to the surface 15, and effluent removal of the used transparent and opaque overlays generated during processing. The umbilical chord from the central robot to a primary laser source 12 and controller 16 can provide laser beam delivery as well as providing other utilities to the robot while it traverses its search surface.

The present laser search peening as described overcomes the long preparation times needed for previous exfoliation corrosion searches, such as by glass bead shot peening. Previously a tent needed to be erected about the structure to be search peened, such as a wing, to contain the glass bead media. After search peening was completed, the glass bead media needed to be removed from the exposed surface of the wing. In the present laser search peening system, only a small volume of the wing's surface on an aircraft needs to be enclosed to contain the laser beam and the processing materials. Additionally, the process materials, such as the used transparent and opaque overlay can be removed from the wings surface during the process, thereby significantly reducing the cleanup time. The entire wing structure therefore, does not need to be isolated from the rest of the processing facility during use of the processing equipment.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for detecting exfoliation corrosion on a surface comprising the steps of:
    defining an area on the surface for corrosion inspection;
    applying an overlay to the surface of said area;
    projecting a laser beam on a portion of said area, said laser beam forming a laser spot and generating a pressure pulse and resulting compressive residual stresses; and
    examining the area of said surface for evidence of exfoliation corrosion.

2. The method of claim 1, wherein said overlay is transparent to said laser beam.

3. The method of claim 1, further comprised of applying a second overlay wherein said second overlay is opaque.

4. The method of claim 3, wherein said opaque overlay is tape.

5. The method of claim 3, wherein said opaque overlay is paint.

6. The method of claim 1, wherein said area for inspection is a machined edge of the surface.

7. The method of claim 1, wherein said area for inspection is made of aluminum, said aluminum includes one of a hole or machined edge.

8. The method of claim 1, wherein said laser beam generates a power density from 0.5 to 9 GW/cm$^2$.

9. The method of claim 1, wherein said laser beam source is fired at a rate of 1 to 100 hertz.

10. The method of claim 1, wherein a plurality of said laser spots are applied in a series of concentric shapes.

11. The method of claim 1, wherein said laser beam spot is formed in one of an elliptical shape or spiral shape.

12. The method of claim 1, wherein said laser beam spot is formed in a circular shape.

13. The method of claim 1, wherein said laser beam spot is formed in a square shape.

14. A method for detecting exfoliation corrosion on a workpiece, said method comprising the steps of:
    defining a first area on the workpiece for surface corrosion inspection;
    applying a transparent and opaque overlay to said area;
    projecting a laser beam on a second area on the workpiece, said laser beam forming a laser spot and generating a pressure pulse and resulting compressive residual stresses on an area of said surface;
    examining said first area of said surface for evidence of exfoliation corrosion; and
    removing said exfoliation corrosion once detected.

15. A method for detecting exfoliation corrosion on a surface comprising the steps of:
    defining an area on said surface for surface corrosion analysis;
    applying a transparent and opaque overlay to the surface of said area;
    projecting a laser beam on said surface, said laser beam forming a laser beam spot and generating a pressure pulse and resulting compressive residual stresses on said surface;
    examining said area of said surface for evidence of exfoliation corrosion; and moving the laser beam along the surface of the part being pulsed.

16. The method in claim 15, wherein moving said laser beam along the surface is performed by a robot.

17. The method in claim 16, wherein said robot is successively indexed from a first area where exfoliation corrosion may exist to a second area where exfoliation corrosion may exist.

18. The method of claim 1, further comprised of directing the said laser beam to provide a plurality of laser beam spots within said area.

19. The method of claim 18, wherein said plurality of said laser beam spots is applied in a specific pattern in said area.

20. The method of claim 1, wherein said examining area of said surface for evidence of said exfoliation corrosion is performed with an optical imaging system.

21. The method of claim 14, further comprised of repeating said steps until the exfoliation corrosion is removed.

22. The method of claim 1, wherein said steps are sequentially activated by a controller.

* * * * *

UNITED STATES PATENT AND TRADEMARK OFFICE
CERTIFICATE OF CORRECTION

| | | |
|---|---|---|
| PATENT NO. | : 6,528,763 B1 | |
| APPLICATION NO. | : 09/846084 | |
| DATED | : March 4, 2003 | |
| INVENTOR(S) | : David F. Lahrman, Allan H. Clauer and Jeff L. Dulaney | |

It is certified that error appears in the above-identified patent and that said Letters Patent is hereby corrected as shown below:

Title Page Item [75] The First Listed Inventor's Last Name is Correctly Spelled --Lahrman--.

Signed and Sealed this

Tenth Day of April, 2007

JON W. DUDAS
*Director of the United States Patent and Trademark Office*